United States Patent [19]

Hathway

[11] 4,025,573
[45] May 24, 1977

[54] SEPARATION PROCESS

[75] Inventor: John Trevor Hathway, Middlesbrough, England

[73] Assignee: Imperial Chemical Industries Limited, London, England

[22] Filed: Nov. 13, 1975

[21] Appl. No.: 631,607

[30] Foreign Application Priority Data

Nov. 21, 1974 United Kingdom ............ 50444/74

[52] U.S. Cl. ............................... 260/674 A; 62/532
[51] Int. Cl.² ........................................... C07C 7/14
[58] Field of Search ............. 260/674 A; 62/58 XY

[56] References Cited

UNITED STATES PATENTS

| | | | |
|---|---|---|---|
| 3,544,646 | 12/1970 | Brougton et al. | 260/674 A |
| 3,643,453 | 2/1972 | Groothuis et al. | 260/674 A |
| 3,758,601 | 9/1973 | Wylie | 260/674 A |
| 3,798,282 | 3/1974 | Bemis et al. | 260/674 A |

Primary Examiner—C. Davis
Attorney, Agent, or Firm—Cushman, Darby & Cushman

[57] ABSTRACT

Para-xylene is obtained from a eutectic mixture by chilling the mixture and separating the resulting crystals by crystal classification.

10 Claims, 1 Drawing Figure

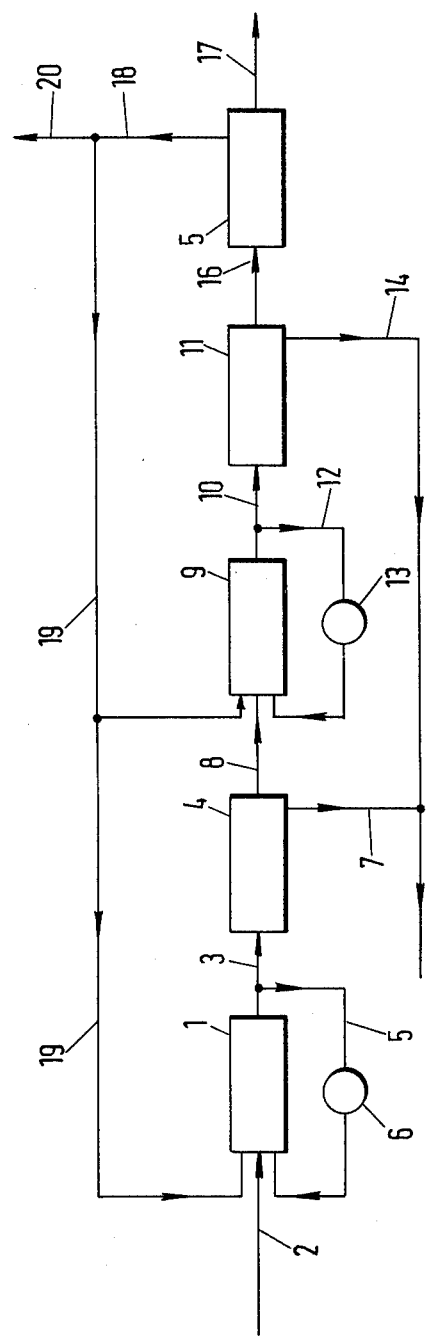

SEPARATION PROCESS

This invention relates to a separation process. Para-xylene is now produced in large quantities at many plants throughout the world. The methods of production employed to make this chemical usually produce a mixture of it with one or more of the other two xylene isomers and/or ethylbenzene. Para-xylene is the most widely used of these four compounds and consequently processes have been developed which attempt to efficiently separate it from the other three compounds. Processes have also been developed to increase the yield of p-xylene by isomerisation of the co-produced o-xylene, m-xylene and ethylbenzene.

It is relatively easy to separate o-xylene and ethylbenzene from their mixtures with p-xylene and m-xylene by fractional distillation. However, the difference in boiling point between p-xylene and m-xylene is only 0.8° C and separation of these two isomers by fractional distillation is impractical. Fortunately, the two isomers can be separated relatively successfully by fractional crystallisation. Processes have been developed, therefore, based on fractional crystallisation alone or on a combination of fractional crystallisation and fractional distillation. However, even fractional crystallisation has its difficulties and disadvantages. Mixtures of xylene isomers, with or without the presence of ethylbenzene, tend to form eutectic mixtures when they are subjected to fractional crystallisation. Thus, although it may be possible to separate a large proportion of the p-xylene from a mixture containing it, a significant amount of p-xylene will remain in the mother liquor as a eutectic mixture with one or more of the $C_8$ isomers. For example, the eutectic mixture formed between the three xylene isomers contains 8 to 9% p-xylene. The two-component eutectic mixture formed between para- and meta-xylene contains about 14% of p-xylene.

In addition, because the eutectic mixture is usually passed to an isomerisation reactor to convert the other isomers to p-xylene, the presence of p-xylene in this isomeriser feed inevitably reduces the capacity of the isomerisation reactor for converting the isomers to p-xylene.

We have now surprisingly found that it is possible to separate significantly greater proportions than hitherto of p-xylene from mixtures containing it and one or more of the other $C_8$ alkyl aromatic isomers.

According to the present invention a process for separating para-xylene from a solution or slurry of a mixture comprising para-xylene and at least one other component which is a xylene isomer present in amounts substantially at or close to their eutectic ratios comprises chilling the solution or slurry to form a mixture of crystals and liquid, and separating crystals of para-xylene from crystals of the other component(s) by classifying the crystals according to their respective sizes and/or shapes.

We have found that there are significant differences in crystal size between p-xylene and the other isomers. As a result, in a liquid mixture containing the various isomers the settling rate of p-xylene crystals is significantly different from the settling rates of the other isomers. These differences in physical characteristics enable the crystals of the isomers to be separated from one another according to their respective sizes and/or shapes in suitable equipment by, for example centrifuge, screens, elutriation, settling, and hydrocyclones.

The feedstock for the process of this invention may be any mixture of p-xylene with one or more of the other isomers, in which mixture the components are present in amounts substantially at or close to their eutectic ratios. Preferably, the feedstock is the mother liquor produced in the primary crystallisation stage of a xylenes manufacturing process. Hitherto, this mother liquor has been used as the feedstock for xylenes isomerisation processes. Preferably the feedstock contains the three xylene isomers in substantially their eutectic ratios, viz. p-xylene 5.4 to 8.2%, o-xylene 27.9 to 30.4%, m-xylene 61.4 to 66.7% (all by weight). In the case of a feedstock containing only two of the xylene isomers, for example p-xylene an m-xylene, the isomers are suitable present in substantially their eutectic ratio, viz. p-xylene 12 to 16%, m-xylene 84 to 88% (both by weight). Optionally, the feedstock may contain ethyl benzene, toluene and/or $C_9$ aromatic hydrocarbons.

Preferably, the feedstock is cooled in one or more stages to a temperature in each stage which is in the range −65° to −103° C, resulting in partial crystallisation of all of the xylene isomers present therein. The crystals are then separated in each stage by crystal classification according to the process of the invention. Suitably, in the case of a feedstock containing the three xylene isomers the para-xylene crystals are separated together with mother liquor leaving a mixture of m-xylene and o-xylene crystals. We have found that the latter mixture contains little or no p-xylene. Conveniently, it is passed to an isomeriser for conversion of the m- and o-xylene to p-xylene. Alternatively the m- and o-xylene may be separated from each other by distillation. The slurry of para-xylene crystals and mother liquor may be filtered or centrifuged to recover the para-xylene crystals. The filtrate of mother liquor, enriched in non-xylene isomer components of the feedstock may then be passed for further processing, for example to remove ethylbenzene, benzene, toluene and other aromatic hydrocarbons which may be present.

Preferred forms of the invention comprise processes of two to four stages in which the first stage comprises chilling of the feedstock and separation of crystals formed. In the second stage and in each of the remaining (if any) stages, mother liquor and, optionally, crystals from the immediately preceding stage are chilled followed by separation of crystals. In the case of a two-stage process, the feedstock is chilled in the first stage so as to form a slurry of crystals and mother liquor in which the mother liquor still contains appreciable amounts of para-xylene and at least one of the other xylene isomers. The crystals present in the slurry are separated according to the process of the invention, that is by crystal classification so that the crystals of o- and m-xylene are separated from the crystals of p-xylene and mother liquor. The mother liquor and p-xylene crystals are then passed to the second stage of the process where they are chilled to a lower temperature than that of the first stage of the process. Preferably, the chilling in the second stage is sufficient to cause crystallisation of a large proportion of the para-xylene and meta- and/or ortho-xylene present in the mother liquor from the first stage. The crystals obtained are again separated by crystal classification so that o- and/or m-xylene are separated from the crystals of p-xylene and mother liquor. The o- and/or m-xylene crystals separated in both stages will generally contain little or no p-xylene. Suitably, these crystals are melted and then recycled for isomerisation. The slurry of para-xylene crystals and mother liquor from the second stage may be filtered and the mother liquor, enriched in non-xylenes but which will still contain significant proportions of xylenes, may be treated to recover any ethylbenzene or other aromatic hydrocarbons present therein. The temperature of chilling in the first stage is preferably in the range −65° to −75° C. In the second stage, the temperature of chilling is preferably in the range −75° to −103° C. Processes involving more than two stages may be operated in a similar fashion. The number of stages used depends to some extent on the amount of crystallisable material being handled. The slurries formed in the process become difficult to handle above a certain concentration of solids and so it is the practice to employ a plurality of stages to effect crystallisation and produce slurries which can be handled easily.

Optionally, separation stages employing crystal classification and operated according to the process of this invention may be combined with one or more separation stages employing prior art methods, for example a method employing the supercooling characteristics of the xylene isomers and which allow one isomer, for example para-xylene, to be crystallised and separated while one or more other isomers, for example meta-xylene, remain in solution.

In the process of this invention it is preferred to separate the crystals using a centrifuge, for example a screen-bowl or solid-bowl centrifuge. If the process is operated in a screen-bowl or solid-bowl centrifuge, the ortho- and meta-xylene isomers are deposited against the bowl as a cake which may be removed by a suitable scroll. Substantially all the p-xylene crystals and mother liquor are conveniently removed through the overflow ports of the centrifuge. The para-xylene crystals may subsequently be separated from the mother liquor in a vacuum filter.

One alternative to centrifugation is to separate the crystals by screening methods using any one or more of several proprietary vibrating sieve devices. The recovery of the desired xylene isomer can be controlled by adopting a sieve having an appropriately large or small sieve size. For example in separating para-xylene from a mixture comprising para-xylene, meta-xylene and ethlbenzene, we have found that choosing a suitably large aperture enables almost all the p-xylene crystals to pass through the sieve, accompanied by very small amounts of other crystals. The larger crystals retained on the sieve include virtually no p-xylene crystals.

In one embodiment of the invention an indirect liquid refrigerant which is immiscible with xylenes may be used to assist in chilling the feedstock. The liquid refrigerant may also serve as a medium for suspending the crystals which are formed. A suitable refrigerant is methanol/water. In using a liquid refrigerant, care must be taken to ensure that the refrigerant is used at temperatures above its own freezing point.

One embodiment of the invention will now be described with reference to the accompanying diagram.

In this embodiment feedstock enters a holding stage 1, for example a residence tank or length of pipe, along line 2. The holding stage 1 may be fitted with cooling coils (not shown) and after chilling the feedstock is passed along line 3 to a first screen bowl centrifuge 4. Alternatively, chilling may be effected by passing feedstock along line 5 through heat exchanger 6 and back to the holding stage 1. A suitable heat exchange medium in heat exchanger 6 is low pressure ethylene. In the centrifuge 4 the cake of o- and/or m-xylene which is formed is removed along line 7 to a melter (not shown). The remaining crystals of p-xylene together with mother liquor are passed along line 8 to a second holding stage 9 in which further chilling is effected by cooling coils (not shown). As in the case of holding stage 1, chilling may be effected in holding stage 9 or alternatively by passage of crystals and mother liquor along line 12, through heat exchanger 13 and back to holding stage 9. After chilling, the slurry of crystals is passed along line 10 to a second screen-bowl centrifuge 11. The cake of o- and/or m-xylene which is formed in centrifuge 11 is removed along line 14 to a melter (not shown) and combined with the o- and/or m-xylene removed along line 7 before passage to an isomeriser (not shown). The crystals of p-xylene and the mother liquor are passed to a vacuum filter or centrifuge 15 along line 16. The para-xylene crystals are removed, if necessary for further purification, along line 17. The mother liquor leaves the vacuum filter or centrifuge 15 by line 18. If desired a portion of the mother liquor may be recycled along 19 to the second holding stage 9 and/or to the first holding stage 1 to assist in obtaining an optimim composition for the slurries undergoing chilling. The remaining mother liquor is removed along line 20 for further processing, for example fractionation, to recover its constituents.

In a typical case, a mother liquor from the primary crystallisation stage of a xylenes manufacturing process and comprising a substantially eutectic mixture of the three xylene isomers was passed along line 2 to the chiller 1. The mother had the following composition (all parts by weight):
p-xylene: 8.2%
m-xylene: 56.4%
o-xylene: 26.1% ethylbenzene: 7.0%
non-$C_8$ material: 2.3%

The mother liquor was chilled to −70° C and then passed to the screen bowl centrifuge 4. Para-xylene crystals and mother liquor separated in the centrifuge 4 were passed to the second holding stage 9. The composition of the slurry (i.e. para-xylene + mother liq.) entering holding stage 9 was as follows (all parts by weight):
p-xylene: 13.1%
m-xylene: 48.5%
o-xylene: 23.6%
ethylbenzene: 11.1%
Toluene/$C_9$ aromatics: 3.7%
% p-xylene solids in slurry: 7.0%

The chilled slurry was passed to centrifuge 11 in which the o- and m-xylene crystals were separated from the p-xylene crystals and mother liquor. The mother liquor obtained from vacuum filter or centrifuge 15 contained (all parts by weight):
p-xylene: 4.2%
m-xylene: 37.8%
o-xylene: 17.6%
ethylbenzene: 30.4%
toluene/$C_9$ aromatics: 10.0%

In another embodiment of the invention, a mixture of para-xylene and meta-xylene crystals in ethylbenzene solution was fed to a 160 micron sieve, with facilities to prevent blinding of the sieve by coarse crystals. The apparatus was immersed in methanol /DRIKOLD refrigerant (DRIKOLD is a Registered Trade Mark) and maintained isothermally at −73.2° C. Analysis of the feed, overflow and underflow appears in Table 1.

Table 1

|  | Weight/100 parts feed | Para-xylene (wt %) | Meta-xylene (wt %) | Ethylbenzene (wt %) |
| --- | --- | --- | --- | --- |
| Feed | 100 | 6.9 | 50.8 | 42.3 |
| Underflow | 54 | 7.2 | 45.6 | 46.3 |
| Overflow | 46 | 6.7 | 55.7 | 37.6 |

Further analysis showed that the smaller para-xylene crystals had passed preferentially through the sieve to give a solids-phase in the underflow which contained considerably more paraxylene than the solids fed, as shown in Table 2.

Table 2

|  | Wt % solids present | Wt % para-xylene in solids phase |
| --- | --- | --- |
| Feed | 10.1 | 17.8 |
| Underflow | 1.6 | 96.3 |
| Overflow | 20.0 | 10.5 |

Thus, some 46.3% of the para-xylene solids fed to the sieve were recovered to the underflow, compared with a recovery of only 0.4% to underflow for the meta-xylene crystals in the feed. The recovery of para-xylene to underflow could be further increased by use of a larger aperture sieve.

The recovery of the p-xylene present in the original feedstock by the process of this invention means that the feed requiring isomerisation contains essentially only meta- and/or ortho-xylenes. The load on the isomeriser is therefore considerably reduced. Moreover, as the isomeriser feedstock contains little or no ethylbenzene, p-xylene or heavy ends, feedstock efficiency is improved and the laydown of coke on the isomeriser catalyst may possibly be reduced. In addition, the impurities such as ethylbenzene and heavy ends are removed by distillation of the final mother liquor from the process of the invention. Hitherto, these impurities had to be removed by distillation of the isomeriser product. Hence the load on the final distillation stage has also been considerably reduced and the ethylbenzene mixtures obtained are much more easily purified than hitherto since the xylenes/ethylbenzene mixtures contain more ethylbenzene.

In the case where a new plant for xylenes production is being erected, adoption of the process of the present invention will mean that both the associated isomeriser and distillation facilities can be smaller than would be the case in a conventional plant. If such a new plant is erected alongside an existing conventional plant, capital and operating costs may be saved by integrating the refrigeration systems for the two plants.

I claim:

1. A process for separating para-xylene from a mixture comprising para-xylene and at least one other component which is a xylene isomer present in amounts substantially at or about their eutectic ratios, which process is conducted in at least two stages comprising in the first stage, chilling the feedstock mixture to form a mixture of crystals and liquid, and separating crystals of para-xylene from the crystals of the other component or components, and which comprises, in the remaining stage or successive stages, chilling of the mother liquor from the immediately preceding stage to a temperature which is lower than that of the first stage followed by separation of the crystals formed, separation of the crystals in at least one stage of the process being by classification of the crystals according to their respective sizes, respective shapes or both.

2. A process as claimed in claim 1 in which the feedstock mixture comprises the mother liquor produced in the primary crystallisation stage of a xylene manufacturing process.

3. A process as claimed in claim 1 in which the remaining stage or stages comprises chilling of the mother liquor and crystals from the immediately preceding stage followed by separation of crystals formed.

4. A process as claimed in claim 1 in which chilling is carried out at a temperature in the range −65° to −103° C.

5. A process as claimed in claim 1 in which the process is carried out in two stages, the chilling temperature in the first stage lying in the range of −65° to −75° C and the chilling temperature in the second stage lying in the range −75° to −103° C.

6. A process as claimed in claim 1 in which the mixture comprises ortho-xylene, meta-xylene and para-xylene and para-xylene crystals together with mother liquor are separated in the first stage from the meta-xylene and ortho-xylene crystals.

7. A process as claimed in claim 1 in which separation of crystals of the xylene isomers is effected in a centrifuge, screening apparatus, eluttiation apparatus, settling apparatus or a hydrocyclone.

8. A process as claimed in claim 3 in which the process is effected in two or more stages, in at least one of which stages separation of crystals is effected by crystal classification and in at least one other stage separation of crystals is effected by a method employing the supercooling characteristics of the xylene isomers in which method one isomer is crystallised and separated while one or more other isomers remain in solution.

9. A process as claimed in claim 1 in which an indirect liquid refrigerant is used to assist the chilling.

10. A process as claimed in claim 1 for separating para-xylene from a mixture comprising para-xylene, meta-xylene and orth-oxylene present in amounts substantially at or close to their eutectic ratios, which comprises, in the first stage, chilling the feedstock mixture to a temperature in the range of −65° to −103° C to form a mixture of crystals and liquid, separating crystals of para-xylene from crystals of the other two xylene isomers by classifying the crystals according to their respective sizes, respective shapes, or both, passing the thus-separated crystals of para-xylene together with the mother liquor to a second stage in which the mixture of mother liquor and para-xylene crystals is chilled to a temperature in the range of −65° to −103° C which is lower than that used in the first stage, and separating crystals of para-xylene from crystals of the other two xylene isomers by classifying the crystals according to their respective sizes, respective shapes or both.

* * * * *